United States Patent
Chattopadhyay et al.

(10) Patent No.: US 7,186,702 B2
(45) Date of Patent: Mar. 6, 2007

(54) **METHOD OF TREATING *LEISHMANIASIS* USING METHYL-BETA-CYCLODEXTRIN**

(75) Inventors: Amitabha Chattopadhyay, Hyderabad (IN); Rentala Madhubala, Hyperabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/141,573

(22) Filed: May 31, 2005

(65) Prior Publication Data

US 2005/0227944 A1    Oct. 13, 2005

Related U.S. Application Data

(62) Division of application No. 10/638,956, filed on Aug. 11, 2003, now abandoned.

(60) Provisional application No. 60/402,830, filed on Aug. 12, 2002.

(51) Int. Cl.
*A61K 31/724* (2006.01)

(52) U.S. Cl. .............................. 514/58; 514/44; 424/65; 424/76.4; 424/405; 424/49; 424/400; 430/166; 536/103; 536/24.5

(58) Field of Classification Search ............... 514/58, 514/44; 424/65, 764, 405, 49, 400; 430/166; 510/293; 536/103, 245
See application file for complete search history.

(56) References Cited

U.S. PATENT DOCUMENTS

| 5,470,836 A | 11/1995 | Donno et al. |
| 6,433,023 B1 * | 8/2002 | Callahan et al. ............ 514/706 |
| 6,610,332 B2 * | 8/2003 | Bandyopadhyay et al. . 424/769 |

* cited by examiner

*Primary Examiner*—Shaojia Anna Jiang
*Assistant Examiner*—Devesh Khare
(74) *Attorney, Agent, or Firm*—Ladas & Parry LLP

(57) ABSTRACT

The present invention relates to a composition useful for the treatment of *leishmaniasis* said composition comprising pharmaceutically effective amount of methyl-beta-cyclodextrin, optionally along with other anti-leishmanial agent(s) and/or pharmaceutically acceptable additives, and a method thereof, wherein the said method reduces the cholesterol levels of the plasma membrane of the infected host cells by about 50%.

18 Claims, 4 Drawing Sheets

METHOD OF TREATING *LEISHMANIASIS* USING METHYL-BETA-CYCLODEXTRIN

Figure 1:
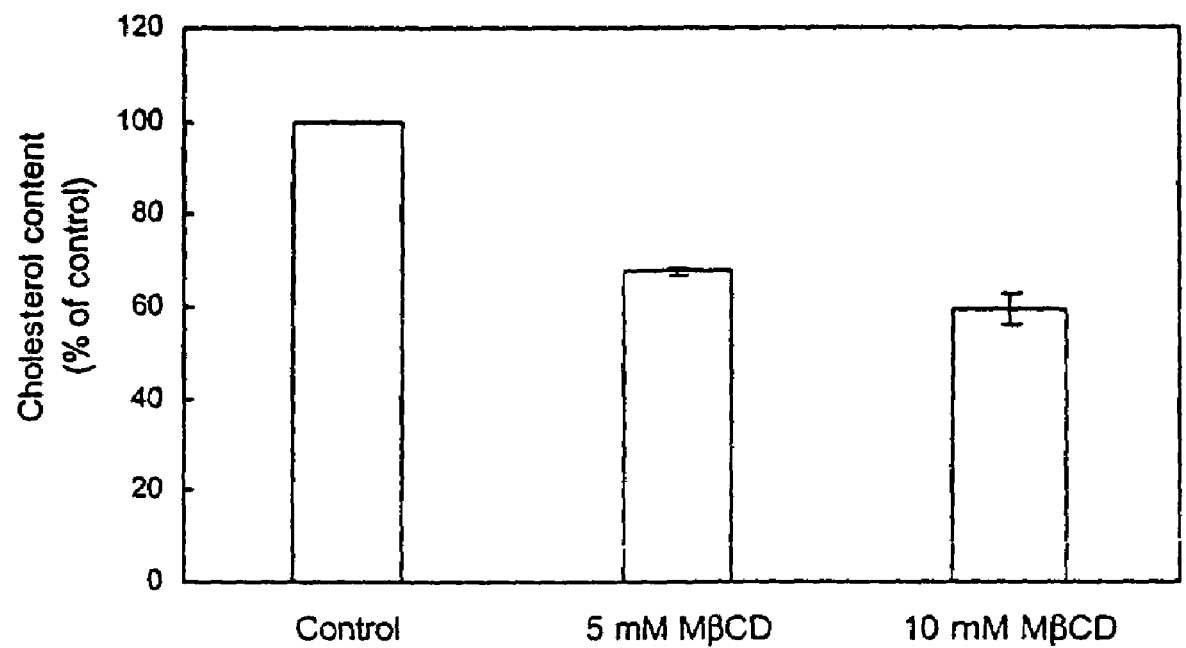

This application is a divisional of application Ser. No. 10/638,956 filed on Aug. 11, 2003 now abandoned, claims the benefit thereof and incorporates the same by reference. The nonprovisional application designated above, namely application 10/638,956, filed Aug. 11, 2003, claims the benefit of U.S. Provisional Application No.: 60/402,830 filed Aug. 12, 2002 and incorporates the same by reference.

FIELD OF THE PRESENT INVENTION

The present invention relates to a composition useful for the treatment of *leishmaniasis* said composition comprising pharmaceutically effective amount of methyl-beta-cyclodextrin, optionally along with other anti-leishmanial agent(s) and/or pharmaceutically acceptable additives, and a method thereof, wherein the said method reduces the cholesterol levels of the plasma membrane of the infected host cells by about 50%.

BACKGROUND AND PRIOR ART OF THE PRESENT INVENTION

*Leishmania* are protozoan parasites that are responsible for substantial public health problems, especially in tropical and subtropical regions. In a recent survey, 88 countries have been declared as leishmaniasis-endemic[7]. The current increase in *leishmaniasis* throughout the world to epidemic proportion coupled with increasing incidence of the disease in developed countries, and emergence of visceral *leishmaniasis* as an important opportunistic infection among people with human immunodeficiency-1 (HIV-1) infection[9] have created an urgency to provide treatment for this intracellular infection. Studies on the molecular mechanisms of parasite entry have led to the identification of several candidate receptors facilitating multiple routes of entry and thus highlighting the redundancy in the entry process. These include macrophage cell surface receptors such as the CR1 and CR3, the mannose-fucose receptor, the fibronectin receptor, the receptor for advanced glycosylation end products, the Fc receptor and the C-reactive protein receptor[8]. However, the large number of different receptors responsible for the attachment and internalization of the parasite to macrophages have contributed to the fact that no single panacea has yet been developed for the treatment of *leishmaniasis*.

OBJECTS OF THE PRESENT INVENTION

The main object of the present invention is to develop a method of treating *leishmaniasis*.

Another main object of the present invention is to develop a method of treating *leishmaniasis*, using methyl-beta-cyclodextrin.

Yet another object of the present invention is to develop a method of using methyl-beta-cyclodextrin in the treatment of *leishmaniasis*.

Still another object of the present invention is to develop a composition comprising methyl-beta-cyclodextrin for the treatment of *leishmaniasis*.

Still another object of the present invention is to develop a treatment regimen for animals including humans, for the management of *leishmaniasis*.

Still another object of the present invention is to develop a safe and efficient composition for the management of *leishmaniasis*.

Still another object of the present invention is to develop a safe and efficient composition comprising methyl-beta-cyclodextrin for the management of *leishmaniasis*.

SUMMARY OF THE PRESENT INVENTION

The present invention relates to a composition useful for the treatment of *leishmaniasis* said composition comprising pharmaceutically effective amount of methyl-beta-cyclodextrin, optionally along with other anti-leishmanial agent(s) and/or pharmaceutically acceptable additives, and a method thereof, wherein the said method reduces the cholesterol levels of the plasma membrane of the infected host cells by about 50%.

DETAILED DESCRIPTION OF THE PRESENT INVENTION

Accordingly, the present invention relates to a composition useful for the treatment of *leishmaniasis* said composition comprising pharmaceutically effective amount of methyl-beta-cyclodextrin, optionally along with other anti-leishmanial agent(s) and/or pharmaceutically acceptable additives, and a method thereof, wherein the said method reduces the cholesterol levels of the plasma membrane of the infected host cells by about 50%.

The main embodiment of the present invention is a method of treating *leishmaniasis* said method consisting of step of administering a composition comprising pharmaceutically effective amount of methyl-beta-cyclodextrin optionally along with other anti-leishmanial agent(s) and/or pharmaceutically acceptable additives, to a subject in need thereof.

In another main embodiment of the present invention, wherein the said method reduces the cholesterol levels of the plasma membrane of the infected host cells by about 50%.

In still another main embodiment of the present invention, wherein said additives are selected from a group of nutrients comprising proteins, carbohydrates, sugar, talc, magnesium stearate, cellulose, calcium carbonate, starch-gelatin paste, and/or pharmaceutically acceptable carrier, excipient, diluent, or solvent.

In still another main embodiment of the present invention, wherein the composition is administered orally, inhaled, or implanted.

In still another main embodiment of the present invention, wherein the composition for the oral route is in form of capsule, tablet, syrup, concentrate, powder, granule, aerosol, and/or beads.

In still another main embodiment of the present invention, wherein the subject is useful animals or human beings.

In still another main embodiment of the present invention, wherein said method shows no adverse effect on subject.

In still another main embodiment of the present invention, wherein the dosage of the methyl-beta-cyclodextrin is ranging between 20 to 500 mg/kg body weight of the subject.

In still another main embodiment of the present invention, wherein the ratio of methyl-beta-cyclodextrin to additives is ranging between 1:10 to 10:1.

In still another main embodiment of the present invention, wherein the said method shows no effect on the other forms of lipids.

In still another main embodiment of the present invention, wherein the anti-leishmanial effect increases with an increase in the amount of methyl-beta-cyclodextrin administered to a subject.

In still another main embodiment of the present invention, wherein the anti-leishmanial effect increases with an increase in the time duration of exposure of methyl-beta-cyclodextrin to a subject.

In another main embodiment of the present invention, wherein a composition useful for the treatment of *leishmaniasis* said composition comprising pharmaceutically effective amount of methyl-beta-cyclodextrin, optionally along with other anti-leishmanial agent(s) and/or pharmaceutically acceptable additives.

In still another main embodiment of the present invention, wherein the concentration of methyl-beta-cyclodextrin is ranging between between 20 to 500 mg/kg body weight of the subject In still another main embodiment of the present invention, wherein the ratio of methyl-beta-cyclodextrin to additives is ranging between 1:10 to 1:1.

In still another main embodiment of the present invention, wherein said additives are selected from a group of nutrients comprising proteins, carbohydrates, sugar, talc, magnesium stearate, cellulose, calcium carbonate, starch-gelatin paste, and/or pharmaceutically acceptable carrier, excipient, diluent, or solvent.

In still another main embodiment of the present invention, wherein the composition is administered orally, inhaled, or implanted.

In still another main embodiment of the present invention, wherein the composition for the oral route is in form of capsule, tablet, syrup, concentrate, powder, granule, aerosol, and/or beads.

Accordingly, the present invention relates to a method of treating *leishmaniasis*, using methyl-beta-cyclodextrin wherein said cyclodextrin depletes cholesterol from the plasma membrane of the cells infected with *Leishmania donovani*.

In an embodiment of the present invention, wherein cholesterol is a major constituent of eukaryotic membranes and plays a crucial role in cellular membrane organization, dynamics, function and sorting[1]. It is often found distributed non-randomly in domains in membranes[2,3]. Recent observations suggest that cholesterol exerts many of its actions by maintaining a specialized type of membrane domain, termed "lipid rafts", in a functional state[4]. The lipid rafts have been implicated as platforms through which signal transduction is coordinated[5] and pathogens gain entry to infect host cells[6].

In another embodiment of the present invention, wherein *Leishmania donovani* is an obligate intracellular parasite that infects macrophages of the vertebrate host resulting in visceral *leishmaniasis* in humans which is usually fatal if untreated[7,8]. The estimated annual number of new cases of *leishmaniasis* is thought to be 2 million[9] and visceral *leishmaniasis* is about 500,000[7]. The molecular mechanisms involved in parasite-host interaction leading to attachment and internalization are poorly characterized. We report here that cholesterol depletion from macrophage plasma membranes using methyl- -cyclodextrin results in a significant reduction in the extent of *leishmanial* infection. Our results show that plasma membrane cholesterol plays a crucial role in efficient attachment and internalization of the parasite to macrophage cells.

In yet another embodiment of the present invention, wherein the objective of the present study was to determine the role of cholesterol in bringing about a productive *leishmanial* infection in mammalian host cells. The murine macrophage cell line J774A.1 was used as a host[10] to a virulent *Leishmania donovani* strain AG83 (MHOM/IN/1983/AG83). Selective cholesterol depletion from the plasma membranes of the host macrophages was achieved by treatment with methyl-cyclodextrin, a compound that specifically extracts cholesterol from the plasma membranes leaving other lipids intact[11,12] and disrupts lipid rafts[13].

In still another embodiment of the present invention, the extent of *leishmanial* infection in control cells and macrophages that were depleted of cholesterol using methyl-β-cyclodextrin (M CD) was assessed at the levels of (i) parasite interaction with the host cell surface as monitored by ligand binding assays using metabolically radiolabeled promastigotes, the extracellular form of the parasites and confirmed by flow cytometric analysis using fluorescently labeled promastigotes and (ii) the eventual presence of the intracellular amastigote form of the parasite in macrophages.

BRIEF DESCRIPTION OF THE ACCOMPANYING DRAWINGS

FIG. 1 shows estimation of cholesterol in control and cholesterol-depleted macrophages. Total cellular cholesterol was estimated using the Amplex Red cholesterol assay kit and shows a concentration-dependent reduction upon treatment with MβCD. The data points shown are the means±standard error of triplicate points from two independent experiments.

Figure 2:
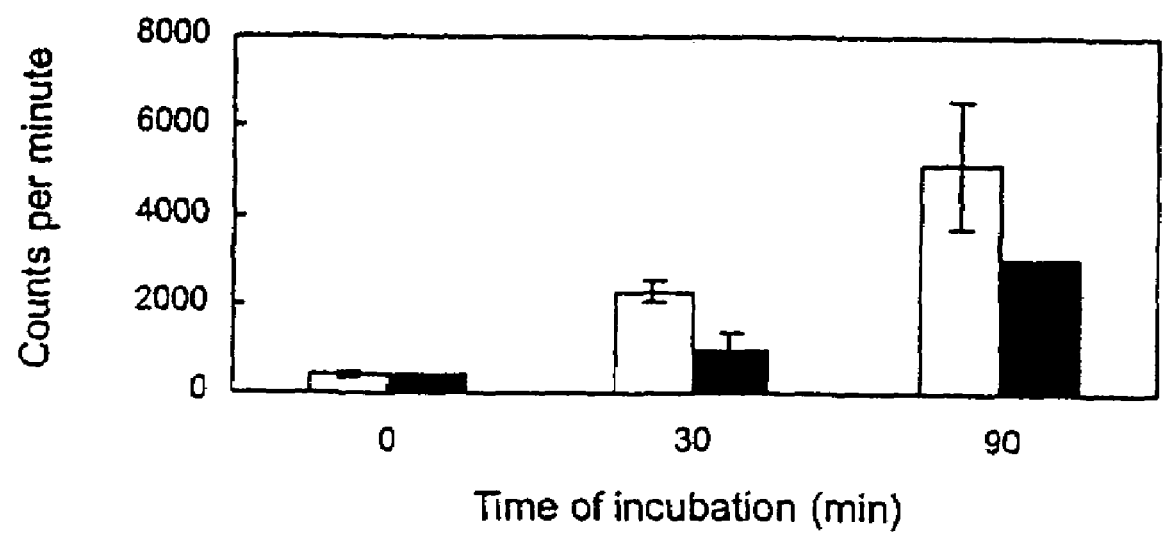

FIG. 2 shows effect of cholesterol depletion using 10 mM MβCD on binding of radiolabeled promastigotes to J774A.1 macrophages. Radiolabeling was carried out as described in Methods and multiplicity of infection was maintained at 10:1 of parasite to macrophage. Comparison of binding of radiolabeled promastigotes between control (white bars) and cholesterol-depleted (black bars) macrophages reveals a reduction in extent and kinetics of binding monitored up to 90 min duration. The data points shown are the means of three independent experiments. The error bars represent the standard error.

Figure 3:
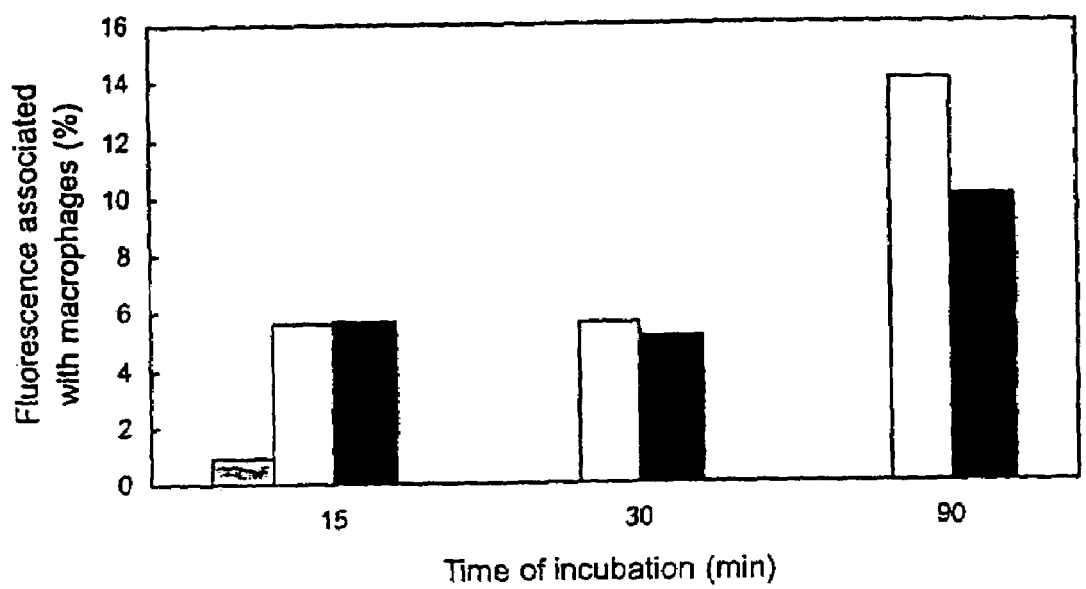

FIG. 3 shows effect of cholesterol depletion on binding of FITC-labeled promastigotes to J774A.1 macrophages monitored by flow cytometry. The concentration of MβCD used was 10 mM. FITC labeling of parasites was carried out as described in Methods. Parasites were added onto the macrophages at a ratio of 10:1. Analysis of representative fluorescence data from macrophages exposed to FITC-labeled parasites for the indicated time periods reveal a pronounced reduction in fluorescence associated with cholesterol-depleted macrophages (black bars) as compared to control macrophages (white bars) especially after 90 min. The gray bar represents fluorescence associated with untreated macrophages exposed to unlabeled parasites.

Figure 4:
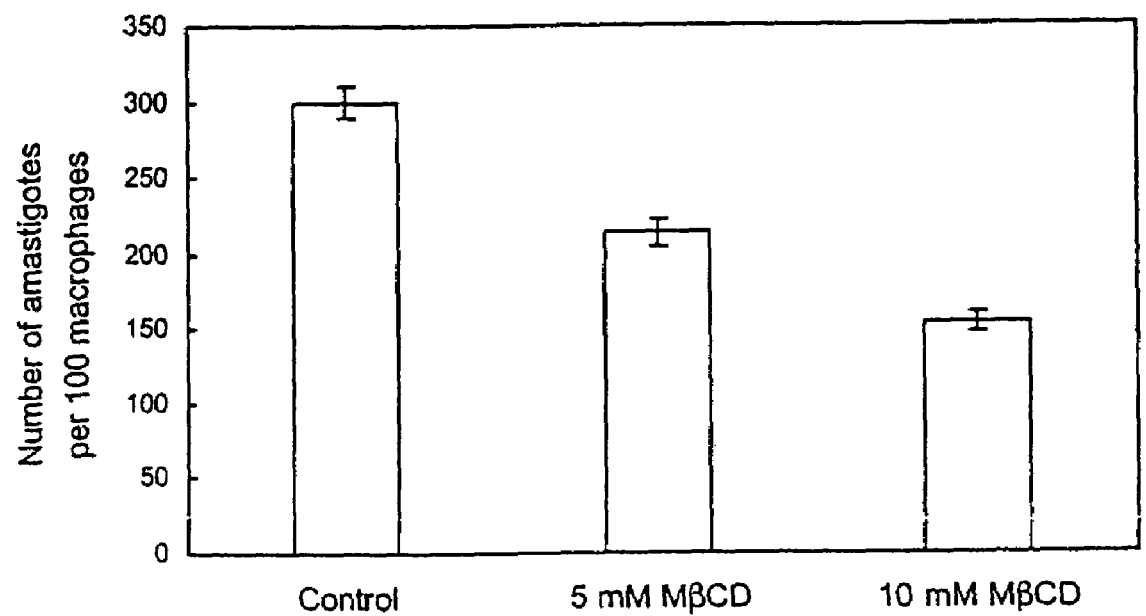

FIG. 4 shows effect of cholesterol depletion on internalization of the parasite assessed by the amastigote count in infected J774A.1 macrophages. Macrophages depleted of cholesterol using 5 and 10 mM MβCD exposed to parasites at multiplicity of infection of 10:1 for 3 hr show a reduction (nearly 50% in the case of 10 mM MβCD treatment) in the number of intracellular amastigotes as revealed by Giemsa staining. The data points shown are the means of six independent experiments. The error bars represent the standard error.

In still another embodiment of the present invention, Cholesterol depletion by treatment with methyl-β-cyclodextrin resulted in a concentration-dependent specific decrease in total cellular cholesterol levels in J774A.1 macrophages as assessed using the Amplex Red cholesterol assay kit with a reduction of ~40% cellular cholesterol when 10 mM methyl-β-cyclodextrin was used (FIG. 1). The concentration of methyl-β-cyclodextrin used for all subsequent experiments was 10 mM except in FIG. 4.

In still another embodiment of the present invention, to analyze the effects of cholesterol depletion on the ability of *Leishmania* parasites to interact with host macrophages, we carried out ligand binding assays with [$^3$H]thymidine labeled promastigotes (FIG. 2). FIG. 2 shows a reduction in kinetics and extent of the host-parasite interaction (attachment) for cholesterol-depleted macrophages compared to control cells when infectivity was assayed till 90 min. Depletion of cholesterol resulted in ~45% reduction in macrophage-parasite interaction when compared to control cells.

In still another embodiment of the present invention, these results were further confirmed by carrying out flow cytometric analysis of FITC-labeled promastigotes. Fluorescent derivatization of promastigotes with FITC has previously been used as a convenient method to accurately monitor host-parasite interaction and provides an ideal means for studying cell surface interaction phenomena since each cell is analyzed individually for its ability to bind to a fluorescent ligand which in this case is FITC-labeled promastigote[14]. Representative data of the fluorescence associated with the macrophages after infection by the parasite is shown in FIG. 3. The data shown in FIG. 3 is representative of two separate experiments with similar results.

In still another embodiment of the present invention, this data supports the earlier conclusions from FIG. 2 that there is a time-dependent reduction in the ability of *leishmania* promastigotes to interact with host cells that are depleted of cholesterol with the effects becoming pronounced as the time of infection is prolonged. Acute cholesterol depletion effects seen in this relatively short time of exposure of the parasites to the macrophages might reflect a phenomenon occurring between the parasite and host cell surfaces like altering recognition or binding events that would have otherwise led to a productive infection. Results from FIGS. 2 and 3 therefore demonstrate that such a loss in cholesterol content is associated with a corresponding loss of attachment and binding of the parasite to host macrophages.

In still another embodiment of the present invention, the above results conclusively demonstrate that cholesterol depletion leads to a reduction in the ability of promastigotes to interact with and bind to host macrophages. For efficient infection, binding of the parasite should be followed by internalization. During the course of infection, the reduced binding of the promastigotes should manifest as a reduction in the intracellular load of amastigotes, the intracellular forms of the parasite present in macrophages. The number of amastigotes was determined visually in infected macrophages that were depleted of cholesterol after staining them with Giemsa. As shown in FIG. 4, treatment of macrophages with methyl-β-cyclodextrin (5 and 10 mM) caused a concomitant reduction in the number of amastigotes present (compared to control cells) in the macrophages with only 50% amastigotes present when depletion was carried out with 10 mM methyl-β-cyclodextrin.

In still another embodiment of the present invention, taken together, our results clearly show that plasma membrane cholesterol plays a crucial role in *leishmanial* infection and cholesterol depletion from macrophages by methyl--cyclodextrin results in a significant reduction in the extent of *leishmanial* infection. We demonstrate this by ligand binding assay using metabolically radiolabeled promastigotes and also by flow cytometric analysis of fluorescently labeled promastigotes. This reduction in binding of the promastigotes to the macrophages is accompanied by a concomitant reduction in the number of the intracellular amastigote form of the parasite.

In still another embodiment of the present invention, the involvement of multiple membrane-bound receptors in the entry of the parasite into host cells has been mentioned earlier[8]. The modulatory role of cholesterol, an essential component in the plasma membranes of eukaryotic cells, on the function of membrane receptors such as the oxytocin receptor[23], galanin receptor[24], and the serotonin$_{1A}$ receptor-$^{Pucadyil,\ T.\ et\ al.,\ unpublished\ observations}$ has been previously demonstrated. These results show that cholesterol depletion may lead to perturbation of receptor-cholesterol interaction leading to loss of receptor function. The reduction in the extent of infectivity of the parasite that is accompanied with cholesterol depletion could be due to such alteration of interaction of receptors responsible for *leishmania* entry into host cells with membrane cholesterol.

In still another embodiment of the present invention, the role of lipid rafts in general and cholesterol in particular is being increasingly recognized in signal transduction[5,15] and entry of pathogens to infect host cells[6]. The involvement of rafts has earlier been shown to control the infection of HIV type 1[16,17], infection of erythrocytes by the malaria parasite *Plasmodium falciparum*[18,19], and entry and internalization of mycobacteria[20,21] and *Brucella suis*[22] into macrophages. However, the nature of infection and the mechanism involved in the management of infection are totally distinct. The source of infections is different and the modes of infecting the host are also totally different. The manifestations of the infection are also distinct. The systems infected by the infection are also distinct. The modes management of the infections is also very distinct. Most importantly, there is no clue to motivate a person skilled in the art to use methyl-beta cyclodextrin for the management of *Leishmaniasis*. Had it been that straight and simple then the management of all the diseases would have been through methyl-beta cyclodextrin. The inventors have put in effort of years and have come out with an innovative method for the management of *Leishmaniasis*.

In still another embodiment of the present invention Cholesterol-mediated entry of *Leishmania* into host cells and reduction in infection may lead to novel therapeutic strategies against *leishmaniasis*. Cyclodextrin-like molecules have earlier been shown to be pharmacologically important in treating unstable atherosclerotic plaques due to their ability to remove cholesterol from macrophage foam cells[25]. Very recently, topical application of -cyclodextrin, a compound analogous to methyl- -cyclodextrin and which selectively extracts cholesterol from plasma membranes, has been shown to block the transmission of cell-associated HIV-1[26]. This is based on earlier observations on the involvement of cholesterol in the infection of HIV type 1[16,17]. Such an application of methyl- -cyclodextrin may block or significantly reduce *leishmanial* infection and further studies in the preclinical and clinical settings are needed to fully explore this issue.

Methods

Cells and cell culture. A murine macrophage cell line J774A.1 (American Type Culture Collection, Rockville, Md.) was used. The cells were maintained at 37° C. in RPMI-1640 medium containing 10% heat inactivated fetal calf serum (FCS)(Biological Industries, Israel) in a $CO_2$ incubator (5% $CO_2$) as described previously[10]. The macrophages were seeded onto tissue culture plates (60 mm) at a density of $1 \times 10^5$ cells/plate and grown for 48 hrs before use.

Parasite culture. *Leishmania donovani* strain AG83 (MHOM/IN/1983/AG83) promastigotes were maintained at 24° C. in modified M-199 medium (Gibco/BRL) supplemented with 100 units/ml penicillin (Sigma, U.S.A.), 100 g/ml streptomycin (Sigma, U.S.A.), and 10% heat inactivated FCS.

Cholesterol depletion and estimation. J774A.1 cells grown on culture dishes were depleted of cholesterol by incubating for 30 min with 5 or 10 mM methyl-β-cyclodextrin (Sigma) at 37° C. in serum free medium[13,23]. Total cellular cholesterol was estimated using Amplex Red cholesterol assay kit[27] (Molecular Probes). Cholesterol values were normalized to protein levels estimated using BCA assay reagent kit[28] (Pierce).

Infecting macrophages with *Leishmania*. Promastigotes were added onto the macrophage monolayers (both control and cholesterol-depleted) at a parasite: macrophage ratio of 10:1. The parasite-macrophage interaction was allowed to progress for 15, 30 and 90 min at 37° C. At the end of incubation, monolayers were washed with phosphate buffered saline (PBS) to remove free parasites and placed on ice to loosen adherent cells from the plates. The monolayers were gently scraped to resuspend the macrophage-parasite complexes and the resulting cell suspension was analyzed either for radiolabel incorporation or macrophage-associated fluorescence. The percentage of infected macrophages was >95% after 3 hr with 5–8 amastigotes per macrophage as determined by Giemsa staining.

Labeling *L. donovani* AG83 promastigotes with tritium or FITC for binding studies. Parasites were metabolically radiolabeled with tritium as described earlier[14] with some modifications. Radiolabel incorporation was carried out at a density of $1 \times 10^7$ cells/2 ml of M-199 medium in the presence of 8 Ci/ml [$^3$H]thymidine (specific activity 89.4 Ci/mmol, New England Nuclear) at 22° C. for 3 hrs. [$^3$H]-labeled promastigotes were co-cultured with the macrophages at a ratio of (10:1) as described above. FITC labeling of parasites was carried out essentially as described previously[29] with minor modifications. Labeling was carried out at 37° C. in PBS. The fluorescence from the FITC-labeled parasites associated with the macrophages was analyzed with a Beckman Coulter ELITE ESP flow cytometer (Miami, Fla.) using EXPO 32 software.

REFERENCES

1. Simons, K. & Ikonen, E. How cells handle cholesterol. *Science* 290, 1721–1726 (2000).
2. Rukmini, R., Rawat, S. S., Biswas, S. C. & Chattopadhyay, A. Cholesterol organization in membranes at low concentrations: effects of curvature stress and membrane thickness. *Biophys. J.* 81, 2122–2134 (2001).
3. Liscum, L. & Underwood, K. W. Intracellular cholesterol transport and compartmentalization. *J. Biol. Chem.* 270, 15443–15446 (1995).
4. Simons, K. & Ikonen, E. Functional rafts in membranes. *Nature* 387, 569–572 (1997).
5. Simons, K. & Toomre, D. Lipid rafts and signal transduction. *Nat. Rev. Mol. Cell Biol.* 1, 31–39 (2000).
6. van der Goot, F. G. & Harder, T. Raft membrane domains: from a liquid-ordered membrane phase to a site of pathogen attack. *Semin. Immunol.* 13, 89–97 (2001).
7. Herwaldt, B. L. *Leishmaniasis Lancet* 354, 1191–1199 (1999).
8. Alexander, J., Satoskar, A. R. & Russell, D. G. *Leishmania* species: models of intracellular parasitism. *J. Cell Sci.* 112, 2993–3002 (1999).
9. Wolday, D., Berhe, N., Akuffo, H. & Britton, S. *Leishmania*-HIV interaction: immunopathogenic mechanisms. *Parasitol. Today* 15, 182–187 (1999).
10. Kapoor, P., Raj, V. S., Saxena, S., Balaraman, S. & Madhubala, R. Effect of *Leishmania donovani* lipophosphoglycan on ornithine decarboxylase activity in macrophages. *J. Parasitol.* 87, 1071–1076 (2001).
11. Kilsdonk, E. P. C. et al. Cellular cholesterol efflux mediated by cyclodextrins. *J. Biol. Chem.* 270, 17250–17256 (1995).
12. Hartel, S., Diehl, H. A. & S. Ojeda, F. Methyl- -cyclodextrins and liposomes as water-soluble carriers for cholesterol incorporation into membranes and its evaluation by a microenzymatic fluorescence assay and membrane fluidity-sensitive dyes. *Anal. Biochem.* 258, 277–284 (1998).
13. Varma, R. & Mayor, S. GPI-anchored proteins are organized in submicron domains at the cell surface. *Nature* 394, 798–801 (1998).
14. Mosser, D. M. & Edelson, P. J. The mouse macrophage receptor for C3bi (CR3) is a major mechanism in the phagocytosis of *leishmania* promastigotes. *J. Immunol.* 135, 2785–2789 (1985).
15. Incardona, J. P. & Eaton, S. Cholesterol in signal transduction. *Curr. Opin. Cell. Biol.* 12, 193–203 (2000).
16. Liao, Z., Cimakasky, L. M., Hampton, R., Nguyen, D. H., & Hildreth, J. E. K. Lipid rafts and HIV pathogenesis: host membrane cholesterol is required for infection by HIV type 1. *AIDS Res. Hum. Retroviruses* 17, 1009–1019 (2001).
17. Campbell, S. M., Crowe, S. M. & Mak, J. Lipid rafts and HIV-1: from viral entry to assembly of progeny virions. *J. Clin. Virol.* 22, 217–227 (2001).
18. Lauer, S. et al. Vacuolar uptake of host components, and a role for cholesterol and sphingomyelin in malarial infection. *EMBO J.* 19, 3556–3564 (2000).
19. Samuel, B. U. et al. The role of cholesterol and glycosylphosphatidylinositol-anchored proteins of erythrocyte rafts in regulating raft protein content and malarial infection. *J. Biol. Chem.* 276, 29319–29329 (2001).
20. Gatfield, J. & Pieters, J. Essential role for cholesterol in entry of mycobacteria into macrophages. *Science* 288, 1647–1650 (2000).
21. Peyron, P., Bordier, C., N'Diaye, E.-N. & Maridonneau-Parini, I. Nonopsonic phagocytosis of *Mycobacterium kansasii* by human neutrophils depends on cholesterol and is mediated by CR3 associated with glycosylphosphatidylinositol-anchored proteins. *J. Immunol.* 165, 5186–5191 (2000).
22. Naroeni, A. & Porte, F. Role of cholesterol and the ganglioside $GM_1$ in entry and short-term survival of *Brucella suis* in murine macrophages. *Infect. Immun.* 70, 1640–1644 (2002).
23. Gimpl, G., Burger, K. & Fahrenholz, F. Cholesterol as modulator of receptor function. *Biochemistry* 36, 10959–10974 (1997).
24. Pang, L., Graziano, M. & Wang, S. Membrane cholesterol modulates galanin-galR2 interaction. *Biochemistry* 38, 12003–12011 (1999).
25. Atger, V. M. et al. Cyclodextrins as catalysts for the removal of cholesterol from macrophage foam cells. *J. Clin. Invest.* 99, 773–780 (1997).
26. Khanna, K. V. et al. Vaginal transmission of cell-associated HIV-1 in the mouse is blocked by a topical, membrane-modifying agent. *J. Clin. Invest.* 109, 205–211 (2002).

27. Amundson, D. M., & Zhou, M. Fluorometric method for the enzymatic determination of cholesterol. *J. Biochem. Biophys. Methods* 38, 43–52 (1999).
28. Smith, P. K. et al. Measurement of protein using bicinchoninic acid. *Anal. Biochem.* 150, 76–85 (1985).
29. Butcher, B. A., Sklar, L. A., Seamer, L. C. & Glew, R. H. Heparin enhances the interaction of infective *Leishmania donovani* promastigotes with mouse peritoneal macrophages: a fluorescence flow cytometric analysis. *J. Immunol.* 148, 2879–2886 (1992).

The invention claimed is:

1. A method of treating *leishmaniasis* comprising administering to a subject in need thereof a pharmaceutically effective amount of methyl-beta-cyclodextrin to treat the *leishmaniasis*.

2. A method as claimed in claim 1, wherein the methyl-beta-cyclodextrin is administered to the patient in the form of a composition comprising the methyl-beta-cyclodextrin and a pharmaceutically acceptable additive or additives, and wherein the composition is administered to the subject in an amount effective to reduce the cholesterol levels of the plasma membrane of infected host cells of the subject by about 50%.

3. A method as claimed in claim 2, wherein the additives comprise a nutrient selected from the group consisting of proteins, carbohydrates, sugar, talc, magnesium stearate, cellulose, calcium carbonate, and starch-gelatin paste.

4. A method as claimed in claim 1, wherein the methyl-beta-cyclodextrin is administered orally, inhaled, or implanted.

5. A method as claimed in claim 2, wherein the composition is administered orally in the form of capsule, tablet, syrup, concentrate, powder, granule, aerosol, or beads.

6. A method as claimed in claim 1, wherein the subject is a human being.

7. A method as claimed in claim 1, wherein the methyl-beta-cyclodextrin is administered to the subject in a dosage of between 20 to 500 mg/kg body weight of the subject.

8. A method as claimed in claim 2, wherein the methyl-beta-cyclodextrin and the additives are present in the composition in a weight ratio of between 1:10 to 10:1.

9. A method as claimed in claim 2, wherein excluding the reduction of the cholesterol levels said method shows no effect on lipids of the subject.

10. In a method for treating *leishmaniasis* comprising administering to a subject in need thereof a composition comprising an anti-leishmanial agent and pharmaceutically acceptable additive or additives, the improvement wherein the composition comprises, in addition to the anti-leishmanial agent and the pharmaceutically acceptable additive or additives, a pharmaceutically effective amount of methyl-beta-cyclodextrin.

11. A method as claimed in claim 10, wherein the composition comprises a concentration of methyl-beta-cyclodextrin between 20 to 500 mg/kg body weight of the subject.

12. A method as claimed in claim 10, wherein the composition comprises a weight ratio of methyl-beta-cyclodextrin to additives of between 1:10 to 10:1.

13. A method as claimed in claim 10, wherein said additives comprise a nutrient selected from the group consisting of proteins, carbohydrates, sugar, talc, magnesium stearate, cellulose, calcium carbonate, and starch-gelatin paste.

14. A method as claimed in claim 10, wherein the composition is administered to the subject orally, inhaled, or implanted.

15. A method as claimed in claim 10, wherein the composition is administered orally to the subject in the form of a capsule, tablet, syrup, concentrate, powder, granule, aerosol, or bead.

16. A method as claimed in claim 3, wherein the composition comprises a pharmaceutically acceptable carrier, excipient, diluent or solvent.

17. A method of treating *leishmaniasis* comprising administering to a subject in need thereof methyl-beta-cyclodextrin in an amount and by a route of administration that reduces cholesterol levels of the plasma membrane of infected host cells of the subject.

18. A method according to claim 17, wherein the route of administration is oral, inhaled, or implanted.

* * * * *